United States Patent [19]
Kalt et al.

[11] Patent Number: 5,904,818
[45] Date of Patent: May 18, 1999

[54] PROCESS FOR THE REGENERATION OF AN AQUEOUS PROCESS LIQUID OF THE AMINE-OXIDE PROCESS

[75] Inventors: Wolfram Kalt, Lenzing; Dieter Eichinger, Vocklabruck; Bruno Mangeng, Seewalchen; Heinrich Firgo, Vocklabruck, all of Austria

[73] Assignee: Lenzing Aktiengesellschaft, Lenzing, Austria

[21] Appl. No.: 08/843,851

[22] Filed: Apr. 17, 1997

Related U.S. Application Data

[63] Continuation-in-part of application No. PCT/AT96/00150, Aug. 16, 1996, and application No. PCT/AT96/00148, Aug. 16, 1996.

[30] Foreign Application Priority Data

Aug. 18, 1995 [AT] Austria ..................................... 1398/95
Aug. 18, 1995 [AT] Austria ..................................... 1400/95

[51] Int. Cl.⁶ ............................. C07D 3/00; C07D 265/30
[52] U.S. Cl. ....................................... 204/157.71; 544/173
[58] Field of Search ....................... 204/157.71; 544/173

[56] References Cited

U.S. PATENT DOCUMENTS

| 4,783,502 | 11/1988 | Faler et al. ............................... 524/871 |
| 5,502,188 | 3/1996 | Massonne et al. ...................... 544/173 |

FOREIGN PATENT DOCUMENTS

| 092862 | 11/1983 | European Pat. Off. . |
| 254803 | 2/1988 | European Pat. Off. . |
| 320690 | 6/1989 | European Pat. Off. . |
| 356419 | 2/1990 | European Pat. Off. . |
| 401503 | 12/1990 | European Pat. Off. . |
| 553070 | 7/1993 | European Pat. Off. . |
| 8808039 | 12/1989 | France . |
| 259863 | 9/1988 | German Dem. Rep. . |
| 4140259 | 6/1993 | Germany . |
| 9511882 | 5/1995 | WIPO . |
| 9707268 | 2/1997 | WIPO . |

OTHER PUBLICATIONS

Shuker et al., Anal. Chem., vol. 55, No. 13, pp. 2152–2155 (1993) (Abstract). No month available.
Buechele et al., J. Anal. Chem., vol. 336, No. 4, pp. 328–332 (1990) (Abstract). No month available.
Conboy et al., Analyst, vol. 114, No. 2, pp. 155–159 (1989, London) (Abstract). No month available.
Rhighezza et al., J. Chromat., vol. 410, pp. 145–155 (1987). No month available.

*Primary Examiner*—Kathryn L. Gorgos
*Assistant Examiner*—Edna Wong
*Attorney, Agent, or Firm*—Baker and Botts, L.L.P

[57] ABSTRACT

The invention is concerned with a process for the production of a solution of N-methylmorpholine-N-oxide in water, characterized by the following steps:

(a) providing an aqueous solution containing N-methylmorpholine and morpholine and exhibiting a pH value of from 6.0 to 9.0, thereafter
(b) treating said aqueous solution with a peroxidic oxidant to oxidize N-methylmorpholine to N-methylmorpholine-N-oxide.

16 Claims, 1 Drawing Sheet

PROCESS FOR THE REGENERATION OF AN AQUEOUS PROCESS LIQUID OF THE AMINE-OXIDE PROCESS

CROSS REFERENCE TO RELATED APPLICATIONS

This application is a continuation-in-part of PCT/AT96/00150 filed Aug. 16, 1996 and PCT/AT96/00148 filed Aug. 16, 1996/, both of which are incorporated by reference herein.

INTRODUCTION

The present invention is concerned with a process for the regeneration of an aqueous process liquid of the amine-oxide process containing N-methylmorpholine and morpholine.

BACKGROUND OF THE INVENTION

For some decades there has been searched for processes for the production of cellulose moulded bodies able to substitute the viscose process, today widely employed. As an alternative which is interesting for its reduced environmental impact among other reasons, it has been found to dissolve cellulose without derivatisation in an organic solvent and extrude from this solution moulded bodies, e.g. fibres, films and other moulded bodies. Fibres thus extruded have received by BISFA (The International Bureau for the Standardization of man made fibers) the generic name Lyocell. By an organic solvent, BISFA understands a mixture of an organic chemical and water.

It has turned out that as an organic solvent, a mixture of a tertiary amine-oxide and water is particularly appropriate for the production of cellulose moulded bodies. As the amine-oxide, primarily N-methylmorpholine-N-oxide (NMMO) is used. Other amine-oxides are described e.g. in EP-A-0 553 070. A process for the production of mouldable cellulose solutions is known e.g. from EP-A-0 356 419. For the purposes of the present specification and the present claims, the production of cellulose moulded bodies using tertiary amine-oxides generally is referred to as amine-oxide process.

In EP-A-0 356 419, an amine-oxide process for the production of spinnable cellulose solutions is described, wherein as a starting material among other substances a suspension of cellulose in liquid, aqueous N-methylmorpholine-N-oxide (NMMO) is used. This process consists in transforming the suspension in a thin-film treatment apparatus in one single step and continuously into a mouldable solution. Finally, the mouldable solution is spun into filaments by a forming tool such as a spinneret and the filaments are passed through a precipitation bath.

In the precipitation bath cellulose is precipitated. The tertiary amine-oxide is accumulated in the precipitation bath. The precipitation bath may contain up to 30 weight % of amine-oxide. For the economy of the amine-oxide process it is of vital importance to recover the amine-oxide as completely as possible and reuse it for the production of a mouldable cellulose solution. Thus it is necessary to recover NMMO from the precipitation bath.

In addition to the amine-oxide however, degradation products of the amine-oxide are also accumulated in the precipitation bath. These degradation products may be intensively coloured, thus deteriorating the quality of the cellulose moulded bodies produced. On the other hand, other substances may represent an additional safety risk, since under certain conditions the amine-oxide tends to show highly exothermic decomposition reactions and these decomposition reactions may be induced or accelerated by certain substances. These substances have to be removed from the precipitation bath which is to be regenerated before the NMMO is concentrated and separated in accordance with the purification process described in WO 97/07268.

After removing these unwanted substances, water is withdrawn from the purified precipitation bath which optionally is combined with other process liquids of the amine-oxide process such as vapour condensates formed during the production of the cellulose solution. This may be carried out for instance by means of evaporation. The residue of this evaporation contains highly concentrated aqueous amine-oxide which is recycled again into the amine-oxide process. The vapours of the evaporation consist mainly of water, wherein significant amounts of N-methylmorpholine, the main degradation product of NMMO, are also dissolved. Moreover, the vapours contain also NMMO and morpholine. Typically, the vapours contain up to 100 mg of NMMO, 240 mg of N-methylmorpholine and 30 mg of morpholine per liter. Conveniently, these vapours are concentrated, e.g., by means of reverse osmosis. The aqueous solution obtained contains typically up to 4 g of NMMO, up to 10 g of N-methylmorpholine and up to approximately 1 g of morpholine.

To keep the NMMO losses as low as possible, it is tried to reoxidize the N-methylmorpholine to NMMO. This may be achieved for instance by means of a peroxidic oxidant.

A process for the preparative production of tertiary amine-oxides by means of oxidation of tertiary amines is known e.g. from EP-A-0 092 862. According to this process, the amine-oxide is oxidized under pressure with molecular oxygen in an aqueous solvent, said solvent having a pH value approximately equal or higher than the pKa value of the tertiary amine.

DD-A-259 863 is concerned with the production of aqueous NMMO solutions by means of oxidation of N-methylmorpholine with $H_2O_2$ and by passing the reaction solution over one or more exchanger columns filled with styrene/divinylbenzene copolymer containing sulphonate groups, as well as by adjusting a pH value of the solution to values ranging from 8 to 5 by addition of phosphoric acid.

In an oxidation it is disadvantageous that morpholine present in the process liquid introduced as a contamination together with the tertiary amines is partially transformed into toxic N-nitrosomorpholine, which is accumulated unwantedly in the NMMO cycle. Additionally, other nitrosoamines are also formed in the oxidation reactions.

Oxidation of N-methylmorpholine with $H_2O_2$ to NMMO is known e.g. from EP-A-0 254 803. From DE-A-4 140 259, the production of NMMO by a process is known wherein the formation of nitrosoamines is restricted by scavenging primary and secondary amines, for instance by means of acid halides. EP-A-0 320 690 describes the production of amine-oxides substantially free from nitrosoamines by oxidation with peroxides in the presence of a combination of $CO_2$/ascorbic acid acting as a nitrosoamine inhibitor. From EP-A-0 401 503, oxidation with $H_2O_2$ in water and a co-solvent, preferably a carboxylic acid ester, is known. According to FR-A-8 808 039, oxidation is carried out while adding $CO_2$, and according to U.S. Pat. No. 5,216,154, oxidation to NMMO is carried out in a pure $CO_2$ atmosphere.

In the state of the art, the forming of nitrosoamine either is not prohibited, or it is achieved by removing the starting products of the N-nitrosomorpholine or by employing additives to slow down the formation rate of the N-nitrosomorpholine. Particularly in an amine-oxide process comprising a closed cycle, the addition of various chemicals such as acid halides or ascorbic acid or $CO_2$ to the process causes problems in the purification of the process liquids, since the degradation products introduced together with the added chemicals have to be removed from the process. For many chemicals, it is also necessary to consider safety aspects such as the risk of exothermic reactions. Thus, neither of the described processes is appropriate for the regeneration of process liquids of the amine-oxide process.

BRIEF SUMMARY OF THE INVENTION

Thus is the objective of the present invention to provide a process for the regeneration of process liquids, wherein N-methylmorpholine is oxidized to NMMO in a simple way, restricting the formation of the toxic N-nitrosomorpholine. This is to be achieved without chemical additives scavenging e.g. morpholine, the starting product for the formation of the N-nitrosomorpholine, for instance by means of derivatisation. Further it is the object of the present invention to carry out this process in such a way that even the reduced amounts of N-nitrosomorpholine formed during oxidation are destroyed to a great extent without chemical additives.

The object to provide a process for the regeneration of process liquids wherein N-methylmorpholine is oxidized to NMMO, the formation of the toxic N-nitrosomorpholine being restricted, is attained by means of a process wherein
(a) an aqueous solution containing N-methylmorpholine and morpholine and having a pH value of from 6.0 to 9.0 is provided, thereafter
(b) said aqueous solution is treated with a peroxidic oxidant to oxidize N-methylmorpholine to N-methylmorpholine-N-oxide.

It has been shown that by simply adjusting the pH of the oxidation mixture within the indicated range it is possible to restrict the formation of the toxic N-nitrosomorpholine and simultaneously attain a maximum oxidation of N-methylmorpholine to NMMO. The pH dependence of these two reaction modes is to be seen from the attached Figures.

BRIEF DESCRIPTION OF THE DRAWINGS

A preferred embodiment of the invention is illustrated in the appended drawings in which.

DETAILED DESCRIPTION OF THE PREFERRED EMBODIMENTS

Figure 1:
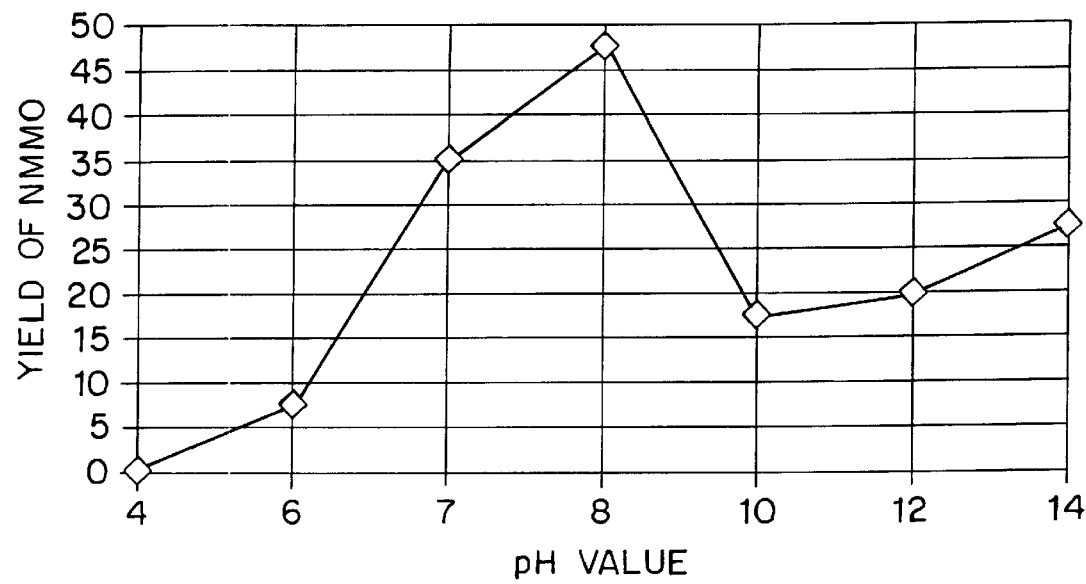
FIG. 1 is a graphical illustration of the yield of N-methylmorpholine-N oxide produced as a function of pH.
Figure 2:
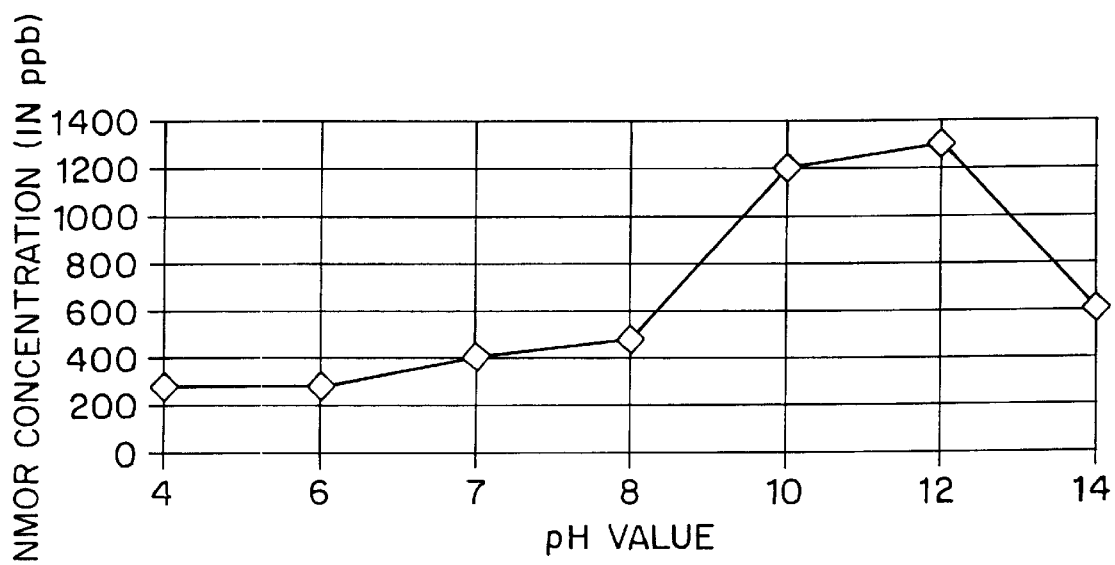
FIG. 2 is a graphical illustration of the amount of N-nitrosomorpholine formed when oxidizing a solution of N-methylmorpholine as a function of pH.

FIG. 1 shows the yield of NMMO produced (% of theory) depending on the pH value of the solution, a maximum being reached in the range of from 6.0 to 9.0 which in the present Example is approximately 50%. FIG. 2 shows the N-nitrosomorpholine concentration (in ppb) in the solution after oxidation depending on the pH value. It can be seen that from a pH value of 8–9 on, the formation of N-nitrosomorpholine increases, reaching a maximum from pH 10 on. By adjusting a pH value according to the invention in the range of from 6.0 to 9.0 in the solution to be oxidized, the yield of NMMO can be maximized and at the same time the formation of the toxic N-nitrosomorpholine can be minimized.

It has proven highly advantageous to adjust the pH value of the aqueous solution within the desired range by passing the solution to be regenerated over a cation exchanger capable of absorbing morpholine. This step provides two important effects regarding the reduction of nitrosoamines. By means of the cation exchanger, morpholine is selectively removed from the solution, thus being actually no morpholine available for the new formation of nitrosoamines. Additionally, by separating the morpholine exhibiting the strongest basicity compared to the other components, the pH value of the solution is lowered precisely into the range wherein the production of NMMO reaches high levels and the formation of nitrosoamines is further inhibited.

Conveniently, the cation exchanger comprises carboxyl groups or sulphonic acid groups.

The object to carry out the process according to the invention such that even the reduced amounts of N-nitrosomorpholine formed during oxidation are destroyed to a great extent without chemical additives may be attained by exposing the aqueous solution during or subsequently to treatment with the peroxidic oxidant to ultraviolet light having substantially a wavelength of 254 nm.

It has been shown that in the preferred embodiment of the process according to the invention to adjust the pH value by means of a cation exchanger, a new formation of N-nitrosomorpholine in the subsequent oxidation actually will not occur, since the pH adjustment is based on the selective removal of morpholine. In this case, the exposure according to the invention fulfils the purpose to destroy a certain basic level of N-nitrosomorpholine present in the process.

Furthermore it has been shown that exposure according to the invention allows a highly efficient destruction of the N-nitrosomorpholine and that the presence of the peroxidic oxidant will not impede that destruction.

The exposure rate may range e.g. from 200 to 500 $mJ/cm^2$, depending on the design of the lamp and the process conditions, particularly the temperature. This embodiment of the process according to the invention does not involve any additional chemicals either.

General methods for the quantitative analysis of nitrosoamines which use a UV exposure and a subsequent determination of the nitrites formed are known (D. E. G. Shuker, S. R. Tannenbaum, Anal. Chem., 1983, 55, 2152–2155; M. Rhighezza, M. H. Murello, A. M. Siouffi, J. Chromat., 1987, 410, 145–155; J. J. Conboy, J. H. Hotchkiss, Analyst, 1989, 114, 155–159; B. Büchele, L. Hoffmann, J. Lang, Fresen. J. Anal. Chem., 1990, 336, 328–333). These analytic methods however do not deal with the destruction of N-nitrosomorpholine.

As the peroxidic oxidant, in the process according to the invention preferably $H_2O_2$ is used. The $H_2O_2$ is employed preferably as an aqueous solution having 30–50 weight % of $H_2O_2$. The $H_2O_2$ is best employed in an amount of from 0.8 to 2 mole per mole of N-methylmorpholine.

The ultraviolet light to which the aqueous solution is exposed is best emitted from a mercury low-pressure lamp. These low-pressure lamps have an intensity maximum at 254 nm.

For exposure according to the invention using a low-pressure lamp, the lamp may be hung into a container containing the process liquid which is to be treated. However the lamp may also be arranged in another way. Moreover, exposure may be carried out for instance during a continuous recycling of the solution to be exposed in a thin-film UV-reactor.

Another preferred embodiment of the process according to the invention comprises the following steps:

(1) passing the above vapours concentrated for instance by means of reverse osmosis over a cation exchanger capable of selectively adsorbing morpholine and safeguarding that the pH value is in the range of from 6.0 to 9.0, thereafter (2) combining the eluate obtained from the cation exchanger with purified precipitation bath of the amine-oxide process, said precipitation bath containing 10–30 weight % of NMMO, and (3) treating the eluate combined with the precipitation bath with the peroxidic oxidant in an evaporation reactor to oxidize N-methylmorpholine and concentrate, obtaining concentrated, aqueous NMMO which is recycled again into the amine-oxide process and vapours which are condensed and employed in step (1).

By means of the following Examples, the invention will be explained in more detail. The abbreviations NMOR, NMMO, NMM and M used in the following denote N-nitrosomorpholine, N-methylmorpholine-N-oxide, N-methylmorpholine and morpholine respectively.

EXAMPLE 1

7 aqueous solutions (50 ml) having 284 ppb of NMOR, containing 6097 mg of NMM, 272 mg of M and 1085 mg of NMMO per liter, were adjusted with HCl/NaOH to the pH values of 4, 6, 7, 8, 10, 12 and 14. Afterwards aqueous hydrogen peroxide having 30 weight % of $H_2O_2$ was added in such an amount as to reach a surplus of 1.3 mole, based on NMM, and heated for 4 hours to 50° C. Subsequently, the yield of newly produced NMMO and the concentration of NMOR was determined by means of HPLC (see Example 2). The results are shown graphically in FIGS. 1 and 2.

In FIG. 1, the pH value is shown as abscissa and the yield of NMMO produced (% of the theory) as ordinate. It can be clearly seen that in the range of from 6.0 to 9.0 there is a maximum of approximately 50%. In FIG. 2, the pH value is also shown as abscissa and the NMOR concentration (in ppb) in the solution after oxidation as ordinate. It can be seen that only from a pH value of from 8–9 formation of N-nitrosomorpholine will considerably increase. Thus in the range of from 6.0 to 9.0 the production of NMMO is maximized and simultaneously the formation of the toxic N-nitrosomorpholine is minimized. This applies particularly to the pH range of between 7.0 and 9.0.

EXAMPLE 2

An aqueous solution containing 25 µg of NMOR, 2530 mg of NMMO, 3923 mg of NMM and 30 mg of M per liter was mixed with 30% $H_2O_2$ (mole of NMM/Mole of $H_2O_2$= 1/1.2) to oxidize NMM to NMMO and exposed to radiation in a UV reactor by means of a mercury low-pressure lamp (of the Katadyn UV projector EK-36, no. 79000 type, made by Katadyn) (wavelength: 254 nm.). The temperature of the process liquid was 50° C.

The NMOR concentration was determined by means of HPLC (column: Hypersil ODS 250×4 mm; 50° C.; eluant: A=0.6% of acetonitrile; B=49.7% of $H_2O$; gradient 1 ml/min., 10 min.—100% A; 7 min.—100% B; detector: UV 238 nm).

Within the first 90 minutes, the NMOR concentration increased to 45 µg/l, which is due to a fast reaction of the M present in the solution. Afterwards however, the NMOR concentration decreased again rapidly. After 6 hours, there was no evidence of NMOR.

After a total oxidation time of 20 hours, the solution contained 5386 mg of NMMO/liter. This amounts to a yield of 62% of theory.

We claim:

1. A process for the production of a solution of N-methylmorpholine-N-oxide in water, comprising the following steps:

(a) providing an aqueous solution comprising N-methylmorpholine and morpholine, the aqueous solution having a pH value of from 6.0 to 9.0, and (b) treating said aqueous solution with a peroxidic oxidant to oxidize N-methylmorpholine to N-methylmorpholine-N-oxide.

2. A process according to claim 1, further comprising the step of passing the aqueous solution in step (a) over a cation exchanger to absorb the morpholine and to adjust the pH value of the aqueous solution.

3. A process according to claim 2, wherein said cation exchanger comprises carboxyl groups.

4. A process according to claim 2, wherein said cation exchanger comprises sulphonic acid groups.

5. A process according to claim 1, 2, 3, or 4, further comprising exposing said aqueous solution to ultraviolet light during treatment with the peroxidic oxidant.

6. A process according to claim 5, wherein said ultraviolet light is emitted from a mercury low-pressure lamp.

7. A process according to claim 6 further comprising exposing said aqueous solution to ultraviolet light subsequently to treatment with the peroxidic oxidant.

8. A process according to claim 5, wherein the ultraviolet light has substantially a wavelength of 254 nm.

9. A process according to claim 8 further comprising exposing said aqueous solution to ultraviolet light subsequently to treatment with the peroxidic oxidant.

10. A process according to claim 5 further comprising exposing said aqueous solution to ultraviolet light subsequently to treatment with the peroxidic oxidant.

11. A process according to claim 1, wherein said aqueous solution comprising morpholine and N-methylmorpholine comprise process liquids from an amine-oxide process.

12. A process according to claim 1, wherein the peroxidic oxidant comprises $H_2O_2$.

13. A process according to claim 1, wherein the peroxidic oxidant comprises an aqueous solution having 30–50 weight % of $H_2O_2$.

14. A process according to claim 1, wherein the peroxidic oxidant is $H_2O_2$ present in an amount of from 0.8 to 2 mole per mole of N-methylmorpholine.

15. A process according to claim 1, wherein the aqueous solution has a pH value of from 7.0 to 9.0.

16. A process according to claims 1, 2, 3, 4, 11, 12, 13, 14, or 15 further comprising exposing said aqueous solution to ultraviolet light subsequently to treatment with the peroxidic oxidant.

* * * * *

UNITED STATES PATENT AND TRADEMARK OFFICE
CERTIFICATE OF CORRECTION

PATENT NO. : 5,904,818

DATED : MAY 18, 1999

INVENTOR(S) : WOLFRAM KALT ET AL.

It is certified that error appears in the above-identified patent and that said Letters Patent is hereby corrected as shown below:

Column 1, line 20: "has" should read --have--;
line 22: "process," should read --process--.

Column 6, line 29, claim 5: "claim" should read --claims--;
line 36, claim 7: "quently" should read --quent--;
line 38, Claim 8: "substantially a wavelength" should read --a wavelength substantially--;
line 41, claim 9: "quently" should read --quent--;
line 44, claim 10: "quently" should read --quent--;
line 47, claim 11: "comprise" should read --comprises--;
line 60, claim 16: "subsequently" should read --subsequent--.

Signed and Sealed this

Third Day of April, 2001

Attest:

NICHOLAS P. GODICI

*Attesting Officer*  *Acting Director of the United States Patent and Trademark Office*